Figure 1:
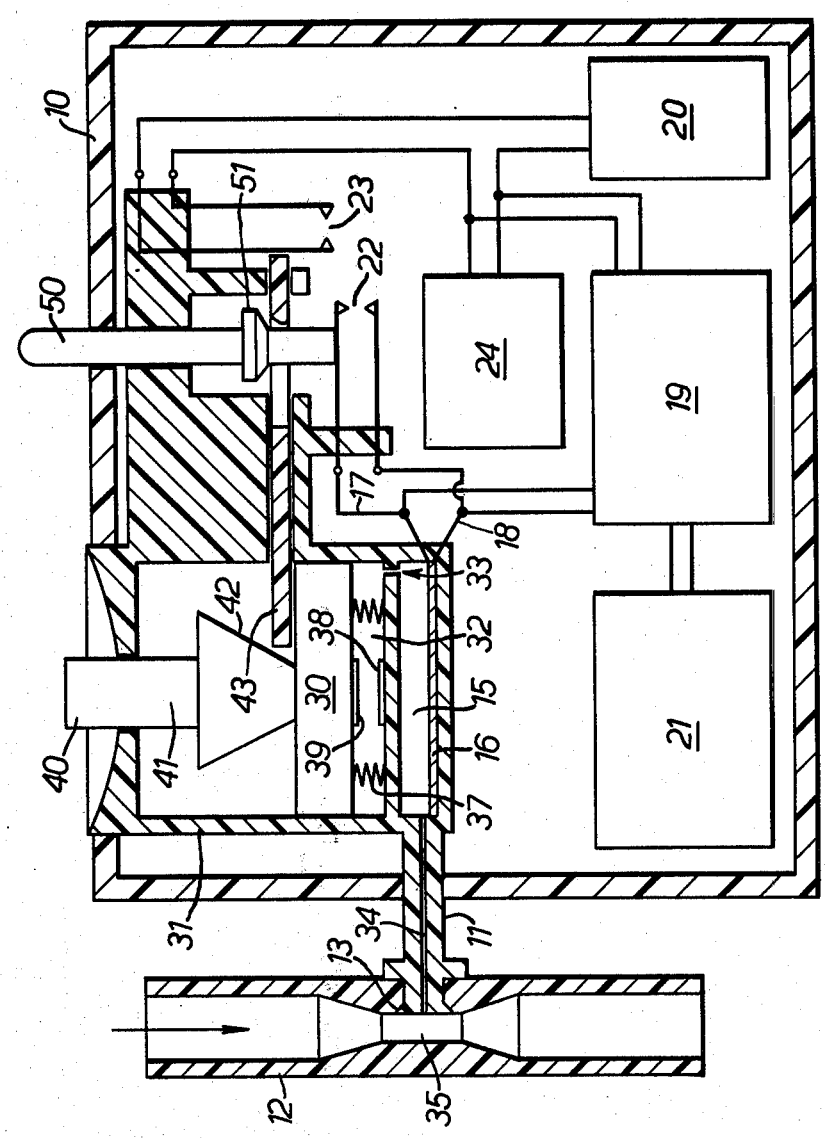

United States Patent [19]

Wright et al.

[11] 4,297,871

[45] Nov. 3, 1981

[54] GAS SAMPLING DEVICES

[76] Inventors: Basil M. Wright, 95, Uxbridge Rd., Rickmansworth, Hertfordshire; Thomas P. Jones, 20, South Rd., Sully, Glamorgan, both of England

[21] Appl. No.: 91,502

[22] Filed: Nov. 5, 1979

[30] Foreign Application Priority Data

Nov. 3, 1978 [GB] United Kingdom ............. 43194/78

[51] Int. Cl.³ ............................................. G01N 1/14
[52] U.S. Cl. ................................... 73/23; 73/863.02; 73/864.62; 128/719; 128/730
[58] Field of Search ..................... 73/421.5 R, 422 R; 128/719, 730

[56] References Cited

U.S. PATENT DOCUMENTS 3,196,689  7/1965  Forrester ....................... 73/421.5 R
3,238,783  3/1966  Wright .......................... 73/421.5 R
3,395,701  8/1968  Bartlett ............................. 128/719
3,661,528  5/1972  Falk .............................. 73/421.5 R

FOREIGN PATENT DOCUMENTS 1203021  10/1965  Fed. Rep. of Germany ..... 73/421.5

Primary Examiner—S. Clement Swisher
Attorney, Agent, or Firm—Young & Thompson

[57] ABSTRACT

A breath sampling device in which a main flow tube through which a subject blows is provided with a venturi restriction. The main flow tube communicates through a passage at the restriction to pressure sensing, constituent sensing, and expansible sample collecting chamber. A control responsive to pressure change delays the operation of the sampler and sensor until breath flow rate diminishes, thus insuring that sampling and sensing occur near the end of expiration.

14 Claims, 4 Drawing Figures

GAS SAMPLING DEVICES

This invention relates to a gas sampling device for obtaining a sample from a gas stream. The invention is particularly but not exclusively applicable for use with breath alcohol detection or analysis.

When collecting a sample of breath for alcohol analysis as a means of estimating the blood alcohol concentration, it is desirable to collect the sample at a carefully selected stage in the exhalation. In many cases this should be as close as possible to the end of the expiration, which should be as full as the subject can achieve. However, it is not generally possible to make an accurate analysis by relating the stage or timing of the sample to the volume of air exhaled, since this varies according to the size of the subject and the state of the lungs. If the timing of the sample is achieved by an automatic volumetric metering device after a certain volume of breath has been exhaled, the metering device would have to be set to a very small volume level for use with small subjects with poor lung function. The volume setting would then be too small for a healthy, large subject, and the blood alcohol concentration would consequently be under-estimated.

Another difficulty experienced in prior devices is that the moist breath entering the instrument tends to condense and the water droplets, sometimes mixed with liquid alcohol or other impurities, disturb the proper functioning of the instrument.

When such an instrument is to be used by police, it is also desirable that it should be as far as possible fully automatic. If the timing of the sample is decided individually by each police officer, it is possible that errors may occur. On the other hand, it is also important that the instrument should be simple and easy to operate and as far as possible foolproof.

It has aleady been proposed to construct a breath sampling device operated automatically by a combination of a positive pressure switch acting on a pre-set delay timer circuit. This, however, suffers from many of the disadvantages mentioned above. The present invention is based on the concept of using a change in pressure in a main gas flow tube to initiate the sampling process.

According to the invention there is provided a gas sampling device for use in apparatus for detecting a constituent in a gas, comprising a displacement element in the form of a movable piston or diaphragm arranged to draw a sample of gas through an inlet passage into a sampling chamber, the displacement element being automatically displaceable from an actuating position in response to a change in gas pressure or a change in flow rate in the inlet passage so as to draw a sample of gas into the chamber.

When a suspect breathes into the main flow tube the rate of flow will rise and then after a period it will fall. The sampling device of the present invention can be designed to trigger the displacement element automatically when the rate starts to fall. In this way the sample is taken at a late stage in the exhaling of the breath so that the test is applied to the alveolar breath, from the deep lung.

Preferably the device includes a venturi in the main flow passage to generate suction which acts on the displacement element. Thus, when the flow rate falls, the suction is reduced, and the displacement element is released. This avoids having excessive quantities of moist gas entering the instrument itself.

The displacement element is preferably spring biased away from the actuating position and is latched in the actuating position with the spring pre-stressed, for example by means of magnets or a mechanical latch or detent. Thus, the displacement element moves rapidly when it is automatically released.

The sampling chamber, or an associated chamber contains a gas detector or sensor which may, for example, be a fuel cell for generating an electric potential dependent upon the quantity of alcohol in the gas sample. When applied to a breath testing instrument the gas detector is coupled to an electrical output or display element. The device may be so constructed that the displacement element is moved manually into its actuating position and then released automatically by the change in gas pressure or the change in the gas flow rate. Alternatively, the displacement element may be moved into the actuating position, and subsequently released therefrom by a change in the gas pressure or the gas flow rate.

Figure 2:
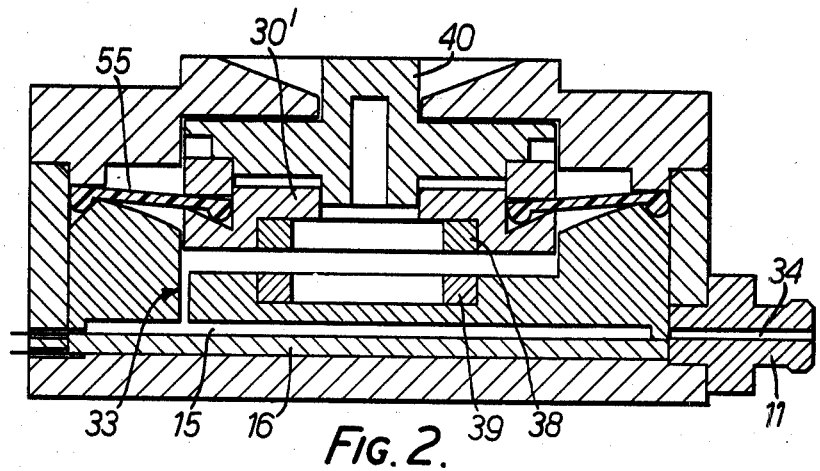
Figure 3:
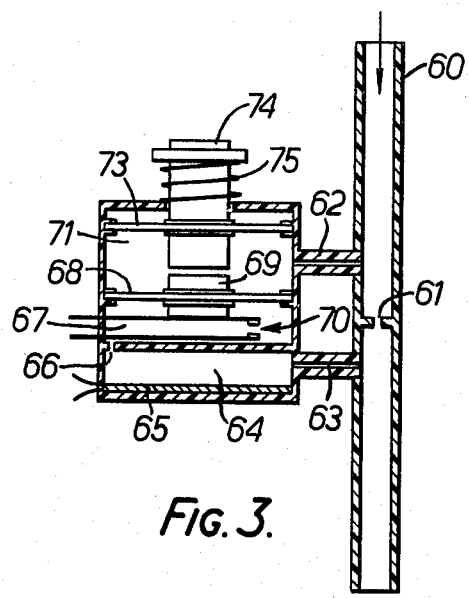
Figure 4:
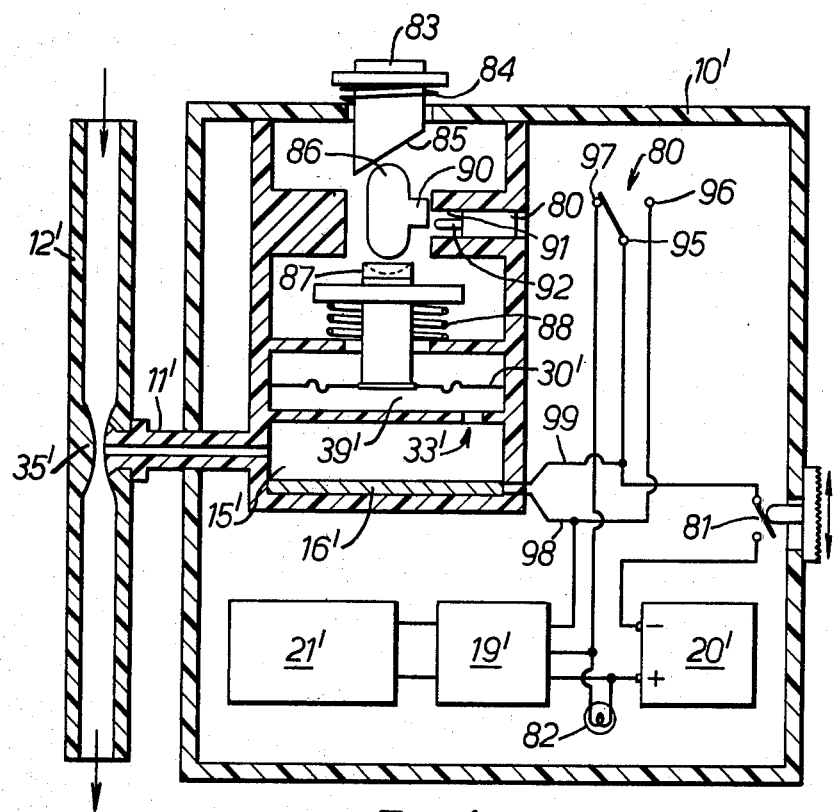

The invention may be performed in various ways and one specific embodiment, with a number of possible modifications, will now be described by way of example with reference to the accompanying drawings, in which:

FIG. 1 is a diagrammatic sectional view through a portable breath testing instrument according to the invention, FIG. 2 is another sectional view illustrating a particular structural form of the gas sampling mechanism, and FIGS. 3 and 4 are diagrammatic sectional views illustrating two further embodiments.

The instrument illustrated in FIG. 1 is intended primarily as a breath testing instrument for use by police officers as a screening test for suspected offenders against alcoholic drinking laws. The instrument comprises a case 10 with a projecting sample tube 11 to which a replaceable plastics breathing tube 12 can be secured as a snap fit on the head 13. The case 10 contains a volumetric sampling mechanism for drawing a sample of breath from the tube 12, and means for indicating the quantity of alcohol per unit volume of the sample.

The sampling mechanism includes a cavity 15 of predetermined volume with a thin flat fuel cell 16 mounted in the base, the fuel cell being for example of the type described in British Pat. No. 1,448,557. The cell has two electrodes between which a potential is generated depending upon the quantity of alcohol present. These electrodes are connected via leads 17, 18 to an amplifier 19 which is energised from internal batteries 20 and has an output connected to a digital or analog or other display unit 21. The lead 17 includes a shorting switch 22 which when closed interconnects the two electrodes to discharge any potential on the fuel cell. The electrical circuitry also includes a switch 23 arranged in the input to the amplifier 19 and coupled to a lamp circuit 24 which indicates when the amplifier and display unit are energised.

The volume sampling device includes a movable piston 30 within a chamber 31, the cavity 32 below the piston communicating via a small port 33 with the chamber 15 above the fuel cell. This same chamber 15 communicates via the passage 34 within the duct 11 with the throat 35 of a venturi constriction formed within the plastics breathing tube 12. A spring 37 urges the piston 30 upwards and a pair of permanent magnets 38, 39 act as a latch or detent to hold the piston down when it reaches the bottom of its travel. A manual button 40 attached to the piston projects through an opening in the adjacent wall of the casing, and the stem 41 of the button is formed with an enlarged cam 42 having an inclined lower surface to co-operate with a sliding catch 43 for a purpose to be described.

The sampling device as so far described operates on the principle that when a suspect blows through the tube 12 there will be a reduction in pressure at the throat 35 of the venturi and this suction pressure will be exerted via the port 33 on the under-face of the piston, which will therefore be drawn down until the magnets engage and latch. The piston will remain in this latched position until the rate of flow through the mouthpiece falls below a predetermined value, which normally corresponds with a late stage in exhaling. When the rate of flow drops, the pressure at the throat of the venturi will rise and at a preselected value the spring 37 will overcome the attraction of the magnets and the piston is urged rapidly upwards, drawing a predetermined volume sample into the chamber 32 via the fuel cell cavity 15. It will be appreciated that when the piston is latched downwards the spring 37 is pre-stressed so that this sampling, which is quite automatically initiated, is very rapid. With the breath sample in the chamber 15, the fuel cell 16 will then react to develop a potential that is amplified and displayed by the units 19, 21.

After each testing sequence it is important that the fuel cell should be discharged to provide a true zero for the next test and it is also important that the battery 20 should not be discharged accidentally. For this purpose the instrument includes a second manual shorting button 50 whose lower end engages one of the spring contacts of the shorting switch 22. The stem of this button 50 has a catch formation 51 which co-operates with a hole in a sliding latch 43. The tip of this latch 43 engages one spring contact of the on/off supply switch 23.

When the main sampling button 40 is depressed the cam surface 42 moves the latch 43 laterally, which closes the on/off supply switch 23 and thus switches on the lamp 24. This also happens if the piston 30 is drawn down by a reduction in pressure at the throat 35 of the venturi. In this position of the latch 43 the shorting button 50 can be depressed, thus closing the shorting switch contacts 22. If the sampling button 40 is released, the head 51 on the stem of the shorting button is then dropped below the latch 43 and will remain so until the sampling button 40 is depressed again, at which stage the latch 43 is shifted again to the right and the shorting button is raised by the spring contacts 22, which are left open. When the sampling button 40 is released the on/off switch 23 opens. A gas sample can then be taken automatically as described above, and a reading is taken later by pressing the button 40 to close contacts 23.

In the practical construction of FIG. 2, like parts are indicated by the same reference numerals with a suffix. In this case the movable piston 30' is attached to an annular diaphragm 55 which acts as a positive fluid seal and also as a natural spring replacing the spring 37 of FIG. 1. It will be noted that this diaphragm is substantially flat and undistorted in the upper position of the piston 30' and will be stressed and distorted when the piston is moved downwards. The diaphragm is, in fact, slightly stressed even in its upper position as illustrated and therefore the piston 30' will move between two well-defined positions. The faces of the components, over which the diaphragm is stressed, are profiled to fit the diaphragm accurately and eliminate dead spots.

In the alternative form of sampling system illustrated in FIG. 3, a detachable breathing tube 60 is formed with an internal constriction 61 in place of a venturi throat. The body of the instrument (not illustrated) has two small tubes or pipes 62, 63 which communicate with the breathing tube on opposite sides of the constriction. The tube 63 leads to a volumetric sampling chamber 64 in which is fitted a fuel cell 65. This chamber communicates via a small port 66 with a further chamber 67 defined partly by a diaphragm 68. A central button 69 on this diaphragm is arranged to engage one spring contact of a switch 70. Above the diaphragm 68 the chamber 71 communicates with the second tube 62 and this is closed off by a second diaphragm 73 connected to a manual sampling button 74 connected by a compression spring 75. When a suspect blows down the tube 60 there will be an increased pressure above the constriction 61 and this will be exerted on the upper face of the diaphragm 68 to shift the diaphragm downwards and close the shorting switch 70. When the suspect's rate of flow falls, near the end of the exhalation, the relative pressure on the upstream side of the constriction drops and the natural resilience in the diaphragm 68 causes it to move upwards, thus drawing a sample into the fuel cell chamber 64 via the tube 63. This is entirely automatic but if it is desired to test the breath for example of an unconscious patient, the manual button 74 can be depressed and released to draw a sample into the fuel cell chamber.

In the further embodiment illustrated in FIG. 4, the instrument is likewise intended primarily for breath testing and the sampling device is designed to be set or "cocked" manually and to be released or activated automatically in response to a decrease in the flow rate through a breathing tube.

In FIG. 4 parts corresponding to the parts in the example of FIG. 1 are indicated by the same reference numerals with an added suffix.

A detachable tube 12' is formed with an internal venturi throat 35' to be connected to a tube 11 projecting from the case 10' of the instrument 11'. This tube 11' leads to a volumetric sampling chamber 15' above a fuel cell 16', this chamber communicating via a small port 33' with another suction chamber 32' below a flexible diaphragm 30'. The electrodes of the fuel cell are connected through a two-pole micro switch 80 into the electrical circuit including a battery 20', amplifier 19', and display indicator 21'. In addition, the circuit includes a manual on/off switch 81, and an indicator lamp 82 across the supply to the amplifier.

In this embodiment the sampling system includes a manual setting button 83 urged upwards by a spring 84 and having an inclined cam surface 85 to engage the upper end of a loosely mounted actuating plunger 86. The lower end of the plunger engages a stud 87 rigidly connected to the centre of the diaphragm 30', the diaphragm and stud being urged upwards by a second spring 88. The plunger 86 has a lateral projection 90 designed to fit into a lateral slot 91 in a fixed part of the casing. Within this slot is fitted the micro switch 80 having a projecting spring button 92. The micro switch has a central common contact 95 with one normally open contact 96 and one normally closed contact 97. The switch fulfills two functions, firstly to short circuit the two electrodes 98,99 of the fuel cell before a new reading is taken, and secondly to close the power supply lead to the amplifier 19'.

When the instrument is to be used to test the breath of a suspected drinker, the button 83 is depressed which urges the plunger 86 downwards together with the stud 87 and diaphragm 30'. The cam surface 85 urges the projection 90 into the slot 91. When the button 83 is released the spring 88 urges the stud 87 upwards and the projection 90 is frictionally trapped within the slot 91. The diaphragm 30' is therefore held down in its cocked position.

The suspect is then invited to blow through the tube 12'. In doing so the flow of breath creates suction at the venturi 35' and in the tube 11'. This draws the diaphragm 30' downwards against the spring 88 through a very short distance sufficient only to release the friction between the parts 90 and 91. The spring button 92 on the micro switch then pushes the projection 90 out of the slot 91. The diaphragm 30', however, is held down by the suction pressure existing at the venturi 35'. When the suspect has discharged a substantial volume of breath the flow rate will begin to fall and the suction pressure at the venturi will be reduced (i.e. the absolute pressure will rise). The spring 88 will therefore pull the diaphragm 30' upwards thus drawing a predetermined volumetric sample of breath into the chamber 15', where it will contact the fuel cell 16'. After a reading has been taken, as described below, the whole operation can then be repeated.

The micro switch 80 is normally disconnected from the projection 90 and the switch contacts 95,97 are normally closed. These contacts are in series with the manual on/off switch 81, and an indicator lamp 82 is connected across the supply to the amplifier 19': when illuminated this shows that the electrical circuit is in the "ready" position. When the button 83 is depressed so that the projection 90 engages the micro switch the contacts 95,97 are opened thus switching off the amplifier and contacts 95,96 are closed thus short circuiting the fuel cell electrode leads 98,99. The fuel cell is thus discharged to provide an accurate zero setting. As soon as the diaphragm 30' moves to draw in a sample of breath the switch 80 returns to its initial position thus removing the short circuit from the fuel cell and again closing the supply to the amplifier.

It will be appreciated that in this embodiment the sampling device is designed to be cocked manually, but to be actuated automatically from the change in flow rate in the breath tube 12'.

We claim:

1. A breath sampling and testing device, comprising a sampling chamber, detector means for detecting a constituent of the gas in said chamber, an open ended breathing tube having a branch passage, a gas displacement element associated with a resilient means and arranged to draw a sample of gas through said branch passage into said sampling chamber, means for sensing a reduction in flow rate in said breathing tube, and arranged automatically to release said displacement element so as to draw a sample of gas through said branch passage into said chamber.

2. A sampling device according to claim 1, including latch means for holding said resilient means in a prestressed condition, when said displacement element is in its primed position, such that when released the displacement element is moved rapidly from the primed position to draw a sample of breath into said chamber.

3. A sampling device according to claim 2, in which said latch means includes a magnet.

4. A sampling device according to claim 2, in which said latch means includes a mechanical detent.

5. A sampling device according to claim 1, in which the detector means comprises an electro-chemical fuel cell for providing an electrical output dependent upon the amount of the constituent in the breath sample.

6. A breath testing device according to claim 1, in which the breathing tube is open at both ends and has a venturi restriction, the venturi restriction being connected via the branch passage to said sampling chamber.

7. Apparatus according to claim 1, including a switch actuated automatically by said displacement element in its primed position, and connected to a display indicator, to indicate when said element is primed.

8. A device according to claim 7, including means for automatically short circuiting said detector means when said displacement element is in its primed position.

9. A breath sampling and testing device comprising a sampling chamber, detector means for detecting a constituent of the breath in said chamber, and means for drawing a sample of breath into said chamber from a breathing tube, including a displacement element associated with resilient means and movable between a primed position and a released position, and including means for shifting said displacement element into its primed position in response to a predetermined flow rate through said breathing tube, and means for releasing said displacement element to draw a sample of breath into said sampling chamber.

10. A breath testing device according to claim 9, in which the displacement element is movable in a separate cavity communicating with said breathing tube via said sampling chamber.

11. A breath testing device according to claim 9, in which the sampling chamber contains an electro-chemical detector element for sensing a constituent in the breath sample.

12. A breath testing device according to claim 9, in which the breathing tube is open ended at each end, and the inlet passage is a lateral branch passage from said breathing tube.

13. A breath testing device according to claim 9, in which said breathing tube includes a venturi passage and in which one side of said displacement element communicates with the throat of said passage whereby suction at said throat induces movement of said displacement element.

14. A breath testing device according to claim 9, in which said breathing tube includes a restriction and one side of said displacement element communicates with the upstream side of said restriction whereby pressure upstream of said restriction induces movement of said displacement element.

* * * * *